United States Patent [19]

Offermanns et al.

[11] 4,124,630
[45] Nov. 7, 1978

[54] PROCESS FOR THE PRODUCTION OF CHLOROMETHYL THIOCYANATE

[76] Inventors: Heribert Offermanns, Grünaustrasse 2, 6450 Hanau 9; Werner Schwarze, Leerbachstrasse 117, 6000 Frankfurt; Rudolf Vanheertum, Landwehr 4, 6450 Hanau, all of Germany

[21] Appl. No.: 845,839

[22] Filed: Oct. 26, 1977

[30] Foreign Application Priority Data

Oct. 28, 1976 [DE] Fed. Rep. of Germany ....... 2648965

[51] Int. Cl.² ............................................. C07C 161/02
[52] U.S. Cl. ..................................... 260/454; 424/302
[58] Field of Search ......................................... 260/454

[56] References Cited

U.S. PATENT DOCUMENTS 2,642,353  6/1953  Mowry et al. ....................... 260/454

Primary Examiner—Lewis Gotts
Assistant Examiner—Robert C. Whittenbaugh
Attorney, Agent, or Firm—Cushman, Darby & Cushman

[57] ABSTRACT

Chloromethyl thiocyanate is prepared by reacting bromochloromethane with an alkali or alkaline earth thiocyanate or with ammonium thiocyanate in the presence of water and an onium salt as a catalyst.

15 Claims, No Drawings

PROCESS FOR THE PRODUCTION OF CHLOROMETHYL THIOCYANATE

BACKGROUND OF THE INVENTION

The invention is directed to a process for the production of chloromethyl thiocyanate starting from bromochloromethane and an ammonium, alkali metal or alkaline earth metal thiocyanate.

It is known to produce chloromethyl thiocyanate from bromochloromethane and a thiocyanate wherein to improve the yields a large excess of thiocyanate is used or higher reaction temperatures and high pressures are employed. For the same purpose there have also been used polyols and amides as solvents. In spite of all these endeavors the two phase system reaction goes slowly and incompletely or proceeds with little selectivity so that unsatisfactory yields cannot be avoided (French Pat. No. 1,545,133).

SUMMARY OF THE INVENTION

It has now been found that chloromethyl thiocyanate can be produced by the reaction of bromochloromethane with an alkali metal or alkaline earth metal thiocyanate or ammonium thiocyanate in the presence of water if the reaction is carried out in the presence of an onium salt as a catalyst.

As alkali metal and alkaline earth metal thiocyanates there can be used for example sodium thiocyanate, potassium thiocyanate, lithium thiocyanate, calcium thiocyanate, strontium thiocyanate and barium thiocyanate.

The onium salt catalysts not only make possible the carrying out of the reaction at normal pressure but they even increase the yields and the speed of reaction as can be seen from the working examples. Because of the increased reactivity it is sufficient to react the bromochloromethane with the stoichiometrically required amount of ammonium, alkali metal or alkaline earth metal thiocyanate. It should be understood that slight excess amounts of either reactant can also be added. A recovery of these salts at the end of the reaction is superfluous. The thiocyanate salt is added either completely or only partially dissolved in water. The exact amount of water is not critical. Usually there are employed 1 to 400 parts of thiocyanate per 100 parts of water.

As the onium salts there are preferred the quaternary phosphonium salts and especially the quaternary ammonium salts.

The onium salts have the formula

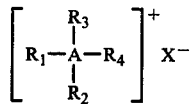

where $X^-$ is for example a halide, e.g., chloride, bromide or iodide, sulfate, sulfonate, nitrate, thiocyanate, cyanide, cyanate, perchlorate, phosphate or hydroxyl ion and A is nitrogen, phosphorus, arsenic, antimony or bismuth. The symbols $R_1$ to $R_4$ can be the same or different and can be aliphatic, e.g., alkyl, aromatic, e.g., phenyl, alkylphenyl or naphthyl, hydroaromatic, e.g., cycloalkyl or heterocyclic, e.g., pyridine, residues which have a total of 4 to 70 carbon atoms. The type of these residues is of minor importance to the successful carrying out of the process of the invention. Of much more importance is that the catalysts added according to the invention have an onium structure and that the anion is dissociated in aqueous solution. The significance of the symbol $X^-$ therefore is not limited to the above-mentioned examples.

The catalysts are used in the reaction in amounts of 0.1 to 20 weight %, preferably 1 to 5 weight % based on the ammonium, alkali metal or alkaline earth metal thiocyanate.

The following compounds are examples of catalysts which can be used in the invention:

benzyl trimethyl ammonium chloride, benzyl triethyl ammonium chloride, butyl tripropyl ammonium bromide, tetrabutyl ammonium iodide, tetrapentyl ammonium iodide, ethyl triphenyl phosphonium bromide, tetraphenyl phosphonium bromide, tetramethyl ammonium chloride, tetramethyl ammonium bromide, tetramethyl ammonium phosphate, tetramethyl ammonium nitrate, dimethyl diethyl ammonium iodide, tetraethyl ammonium iodide, tetrapropyl ammonium iodide, tetradodecyl ammonium iodide, tetraoctadecyl ammonium iodide, tetraphenyl ammonium iodide, tetrabenzyl ammonium iodide, octyl triphenyl ammonium iodide, methyl triphenyl ammonium iodide, dodecyl triphenyl ammonium iodide, phenyl ethyl tetramethylene ammonium iodide, phenyl ethyl pentamethylene ammonium iodide, tetra p-tolyl ammonium iodide, and the corresponding quaternary ammonium chlorides, bromides, sulfates, phosphates and nitrates, e.g., dimethyl diethyl ammonium chloride, tetrapropyl ammonium chloride, tetrapropyl ammonium bromide, tetrabutyl ammonium chloride, tetrabutyl ammonium bromide, tetrabutyl ammonium chloride, tetrabutyl ammonium bromide, tetrabutyl ammonium sulfate, tetraoctyl ammonium chloride, tetraoctyl ammonium bromide, tetrabenzyl ammonium chloride, tetraphenyl ammonium chloride, methyl triphenyl ammonium chloride, phosphonium iodides such as tetramethyl phosphonium iodide, tetraethyl phosphonium iodide, tetrapropyl phosphonium iodide, tetrabutyl phosphonium iodide, tetraisopropyl phosphonium iodide, tetraoctyl phosphonium iodide, tetradodecyl phosphonium iodide, tetraoctadecyl phosphonium iodide, tetraphenyl phosphonium iodide, tetrabenzyl phosphonium iodide, tetra p-tolyl phosphonium iodide, and the corresponding phosphonium chlorides, bromides, sulfates and nitrates, e.g., tetramethyl phosphonium chloride, tetramethyl phosphonium bromide, tetramethyl phosphonium sulfate, tetrabutyl phosphonium chloride, tetrabutyl phosphonium bromide, tetraoctyl phosphonium chloride, tetraphenyl phosphonium chloride, tetraphenyl phosphonium sulfate, tetrabenzyl phosphonium chloride, arsonium salts such as tetramethyl arsonium chloride, tetramethyl arsonium bromide, tetramethyl arsonium iodide, tetramethyl arsonium sulfate, tetrabutyl arsonium chloride, tetraoctyl arsonium chloride, tetraoctyl arsonium bromide, tetraoctyl arsonium iodide, tetraoctyl arsonium sulfate, tetraphenyl arsonium chloride and tetraphenyl arsonium iodide, trimethyl cyclohexyl ammonium chloride, tetracyclohexyl ammonium bromide, trimethyl hexadecyl ammonium chloride, trimethyl hexadecyl ammonium bromide, hexadecyl pyridinium bromide, hexadecyl pyridinium chloride, lauryl pyridinium chloride, trimethyl 2-pyrimidyl ammonium chloride, N-(benzthiazolyl-2-methyl)-pyridiniumperchlorate, dimethyl octyl benzyl ammonium chloride, dimethyl dodecyl benzyl ammonium chloride, dimethyl octadecyl ammonium chloride, tetramethyl ammonium hydroxide, tetraoctyl ammonium hydroxide, trimethyl dodecyl ammonium hydroxide, tetraethyl stibonium chloride, triethyl benzyl stibonium bromide and ethyl triphenyl stibonium chloride.

In carrying out the process of the invention one can so proceed that the catalyst is predissolved either in bromochloromethane or in the aqueous phase, or is added in undissolved form to the reaction mixture. The reaction takes place suitably at elevated temperature, for example, between 50° and 100° C. with intensive mixing of the two phases. The chloromethyl thiocyanate formed is isolated from the organic phase after the end of the reaction is known manner, for example, by distillation.

The chloromethyl thiocyanate has outstanding fungicide, nematocide and bactericide activity. Also, it is useful as a starting material for synthesizing pesticides.

Unless otherwise indicated all parts and percentages are by weight.

The process can comprise, consist essentially of or consist of the steps set forth and the materials can comprise, consist essentially of or consist of those set forth.

DESCRIPTION OF THE PREFERRED EMBODIMENTS

EXAMPLE 1 (COMPARISON EXAMPLE)

There were boiled at reflux under intensive stirring in a three-necked flask 129.5 grams (1 mole) of bromochloromethane and 81.07 grams (1 mole) of sodium thiocyanate as a 40% aqueous solution. Within 17 hours the temperature increased from 65° C. to 77° C. The mixture was allowed to cool and the organic phase separated. This phase was washed with water and subsequently distilled in a vacuum. The chloromethyl thiocyanate (49.5 grams) distilled at 71° C./13 mm Hg. The yield was 46.0% of theory.

EXAMPLE 2

The reaction was carried out as described in Example 1 except 1 gram of benzyl triethyl ammonium chloride was added. The temperature increased within 10 hours to 97° C. There were isolated by distillation from the organic phase 83.9 grams of chloromethyl thiocyanate, corresponding to a yield of 78.0% of theory.

EXAMPLE 3

The reaction was carried out as described in Example 2. However, there were added 4 grams of benzyl triethyl ammonium chloride. The reaction temperature increased within 5.5 hours to 96° C. From the organic phase there were isolated 92.6 grams of chloromethyl thiocyanate, corresponding to a yield of 86.1% of theory.

EXAMPLE 4

129.5 grams of bromochloromethane were boiled at reflux with a solution of 81.1 grams of sodium thiocyanate in 80 grams of water with addition of 3 grams of tetrabutyl ammonium iodide. Within 5 hours a reaction temperature of 97.5° C. was reached. 87.3 grams of chloromethyl thiocyanate were isolated from the organic phase in known manner, corresponding to a yield of 81.2% of theory.

EXAMPLE 5

2 moles of bromochloromethane and 2 moles of sodium thiocyanate dissolved in 200 grams of water were boiled at reflux under intensive stirring. There were added 8 grams of tetraphenyl phosphonium bromide. Within 5.5 hours the reaction temperature increased to 95° C. There were isolated 150 grams of chloromethyl thiocyanate. This corresponds to a yield of 69.8% of theory.

EXAMPLE 6

129.5 grams of bromochloromethane were treated with 76 grams of ammonium thiocyanate dissolved in 100 grams of water. With addition of 4 grams of benzyl triethyl ammonium chloride the mixture was boiled at reflux for 5 hours. The organic phase was washed with water and distilled in a vacuum. There were isolated 76.4 grams of chloromethyl thiocyanate, corresponding to a yield of 71.0% of theory.

EXAMPLE 7

129.5 grams (1 mole) of bromochloromethane were dissolved in 100 grams of water with 105.2 grams (0.5 mole) of calcium thiocyanate trihydrate and treated with 4 grams of benzyl triethyl ammonium chloride. The mixture was boiled at reflux with stirring for 10 hours. The organic phase was washed with water and distilled in a vacuum. There were isolated 78.0 grams of chloromethyl thiocyanate, corresponding to a yield of 72.5% of theory.

What is claimed is:

1. A process for the production of chloromethyl thiocyanate comprising reacting bromochloromethane with ammonium, alkali metal or alkaline earth metal thiocyanate in the presence of water and with an organic onium salt or base as a catalyst.

2. A process according to claim 1 wherein the organic onium salt or base is an ammonium, phosphonium, arsonium or stibonium compound.

3. A process according to claim 1 wherein the catalyst has the formula:

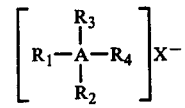

where $R_1$, $R_2$, $R_3$ and $R_4$ are alkyl, phenyl, tolyl, benzyl, cyclohexyl, or $R_1$, $R_2$ and $R_3$ together with A are pyridinium, A is nitrogen, phosphorus, arsenic, antimony or bismuth and $X^-$ is an anion which dissociates in aqueous solution.

4. A process according to claim 3 wherein the total number of carbon atoms in $R_1$, $R_2$, $R_3$ and $R_4$ is 4 to 70.

5. A process according to claim 4 wherein $R_1$, $R_2$, $R_3$ and $R_4$ are alkyl, benzyl, phenyl or tolyl.

6. A process according to claim 3 wherein the catalyst is present in an amount of 0.1 to 20 weight % based on the thiocyanate employed.

7. A process according to claim 6 wherein the thiocyanate employed is ammonium, sodium, potassium or calcium thiocyanate.

8. A process according to claim 6 wherein the catalyst is present in an amount of 1 to 5 weight % based on the thiocyanate employed.

9. A process according to claim 6 wherein the thiocyanate is employed in an amount from a stoichiometric amount to slightly above a stoichiometeric amount.

10. A process according to claim 6 wherein the catalyst is a quaternary phosphonium salt or a quaternary ammonium salt.

11. A process according to claim 10 wherein the salt is a halide.

12. A process according to claim 11 wherein the salt is a quaternary ammonium halide.

13. A process according to claim 11 wherein the halide is a chloride, bromide or iodide.

14. A process according to claim 10 wherein the catalyst is a quaternary ammonium salt.

15. A process according to claim 6 wherein the reaction temperature is 50° to 100° C.

* * * * *